(12) United States Patent
Paul et al.

(10) Patent No.: US 7,879,030 B2
(45) Date of Patent: *Feb. 1, 2011

(54) MULTIPOLAR, VIRTUAL-ELECTRODE CATHETER WITH AT LEAST ONE SURFACE ELECTRODE AND METHOD FOR ABLATION

(75) Inventors: Saurav Paul, Minneapolis, MN (US); Kedar Ravindra Belhe, Minnetonka, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1045 days.

This patent is subject to a terminal disclaimer.

(21) Appl. No.: 11/190,560

(22) Filed: Jul. 27, 2005

(65) Prior Publication Data

US 2007/0027448 A1    Feb. 1, 2007

(51) Int. Cl.
A61B 18/14    (2006.01)
(52) U.S. Cl. .................................. 606/41; 607/105
(58) Field of Classification Search .............. 606/41, 606/32, 34; 607/105
See application file for complete search history.

(56) References Cited

U.S. PATENT DOCUMENTS

| | | | |
|---|---|---|---|
| 4,945,912 A | 8/1990 | Langberg | |
| 5,281,213 A | 1/1994 | Milder et al. | 606/15 |
| 5,281,217 A | 1/1994 | Edwards et al. | 606/41 |
| 5,334,193 A | 8/1994 | Nardella | 6/41 |
| 5,370,644 A | 12/1994 | Langberg | |
| 5,431,649 A | 7/1995 | Mulier et al. | 606/41 |
| 5,433,708 A * | 7/1995 | Nichols et al. | 604/113 |
| 5,472,441 A * | 12/1995 | Edwards et al. | 606/41 |
| 5,542,928 A * | 8/1996 | Evans et al. | 604/113 |
| 5,584,872 A | 12/1996 | LaFontaine et al. | 607/116 |
| 5,609,151 A | 3/1997 | Mulier et al. | 128/642 |
| 5,658,278 A | 8/1997 | Imran et al. | 606/41 |
| 5,676,693 A | 10/1997 | LaFontaine | 607/116 |
| 5,697,927 A | 12/1997 | Imran et al. | 606/41 |
| 5,725,524 A | 3/1998 | Mulier et al. | 606/41 |
| 5,785,706 A | 7/1998 | Bednarek | 606/41 |
| 5,797,905 A * | 8/1998 | Fleischman et al. | 606/41 |

(Continued)

OTHER PUBLICATIONS

PCT International Search Report and Written Opinion of the International Searching Authority for PCT/US06/28912. dated Feb 20, 2007, 8 pages.

*Primary Examiner*—Lee S Cohen
(74) *Attorney, Agent, or Firm*—Heimbecher & Assoc., LLC

(57) ABSTRACT

Virtual-electrode catheters and methods for using such virtual-electrode catheters are disclosed. For example, bipolar and multipolar, virtual-electrode catheters having at least one internal electrode and at least one surface electrode, and methods of using these catheters for treatment of cardiac arrhythmias via, for example, radiofrequency (RF) ablation are disclosed. The catheters may comprise a catheter body with an internal lumen extending within it and adapted to flowingly receive a conductive fluid. An exit feature defining a flow path from the internal lumen to the catheter's outer surface may exist through a sidewall of the catheter body. A conductor is mounted within the internal lumen adjacent to the exit feature and is adapted to deliver treatment energy to the tissue via the conductive fluid in the internal lumen. At least one surface electrode is mounted on the outer surface of the catheter body adjacent to the exit feature.

39 Claims, 10 Drawing Sheets

U.S. PATENT DOCUMENTS

| | | | |
|---|---|---|---|
| 5,800,482 A * | 9/1998 | Pomeranz et al. | 607/101 |
| 5,876,398 A | 3/1999 | Mulier et al. | 606/41 |
| 5,895,417 A * | 4/1999 | Pomeranz et al. | 607/101 |
| 5,913,854 A | 6/1999 | Maguire et al. | 600/41 |
| 5,913,856 A | 6/1999 | Chia et al. | 606/41 |
| 5,919,188 A | 7/1999 | Shearon et al. | 600/41 |
| 5,971,968 A | 10/1999 | Tu et al. | 604/264 |
| 5,997,532 A | 12/1999 | McLaughlin et al. | 606/41 |
| 6,010,500 A | 1/2000 | Sherman et al. | 606/41 |
| 6,015,407 A | 1/2000 | Rieb et al. | 606/101 |
| 6,016,809 A | 1/2000 | Mulier et al. | 128/898 |
| 6,032,077 A | 2/2000 | Pomeranz | 607/101 |
| 6,063,080 A | 5/2000 | Nelson et al. | 606/41 |
| 6,068,653 A | 5/2000 | LaFontaine | 607/116 |
| 6,080,151 A | 6/2000 | Swartz et al. | 606/16 |
| 6,119,041 A | 9/2000 | Pomeranz et al. | 607/101 |
| 6,120,476 A | 9/2000 | Fung et al. | 604/95 |
| 6,120,500 A | 9/2000 | Bednarek et al. | 606/41 |
| 6,132,426 A | 10/2000 | Kroll | 606/41 |
| 6,168,594 B1 | 1/2001 | LaFontaine et al. | 606/41 |
| 6,171,275 B1 | 1/2001 | Webster, Jr. | 604/20 |
| 6,217,576 B1 | 4/2001 | Tu et al. | 606/41 |
| 6,219,582 B1 | 4/2001 | Hofstad et al. | 607/122 |
| 6,235,022 B1 | 5/2001 | Hallock et al. | 606/41 |
| 6,235,044 B1 | 5/2001 | Root et al. | 606/200 |
| 6,238,393 B1 | 5/2001 | Mulier et al. | 606/41 |
| 6,241,722 B1 | 6/2001 | Dobak et al. | 606/23 |
| 6,409,722 B1 | 6/2002 | Hoey et al. | 606/34 |
| 6,454,766 B1 | 9/2002 | Swanson et al. | 606/41 |
| 6,605,087 B2 * | 8/2003 | Swartz et al. | 606/41 |
| 6,702,811 B2 * | 3/2004 | Stewart et al. | 606/41 |
| 6,849,073 B2 | 2/2005 | Hoey et al. | |
| 6,855,143 B2 | 2/2005 | Davison et al. | |
| 6,858,026 B2 | 2/2005 | Sliwa et al. | 606/28 |
| 7,416,552 B2 * | 8/2008 | Paul et al. | 606/41 |
| 7,419,486 B2 * | 9/2008 | Kampa | 606/32 |
| 2002/0026188 A1 * | 2/2002 | Balbierz et al. | 606/41 |
| 2002/0120267 A1 * | 8/2002 | Phan | 606/51 |
| 2003/0212394 A1 * | 11/2003 | Pearson et al. | 606/41 |
| 2004/0059325 A1 * | 3/2004 | Swanson | 606/41 |
| 2004/0147921 A1 * | 7/2004 | Edwards et al. | 606/41 |
| 2004/0181189 A1 | 9/2004 | Roychowdhury et al. | |
| 2004/0215180 A1 | 10/2004 | Starkebaum et al. | |
| 2005/0055019 A1 | 3/2005 | Skarda | |

\* cited by examiner

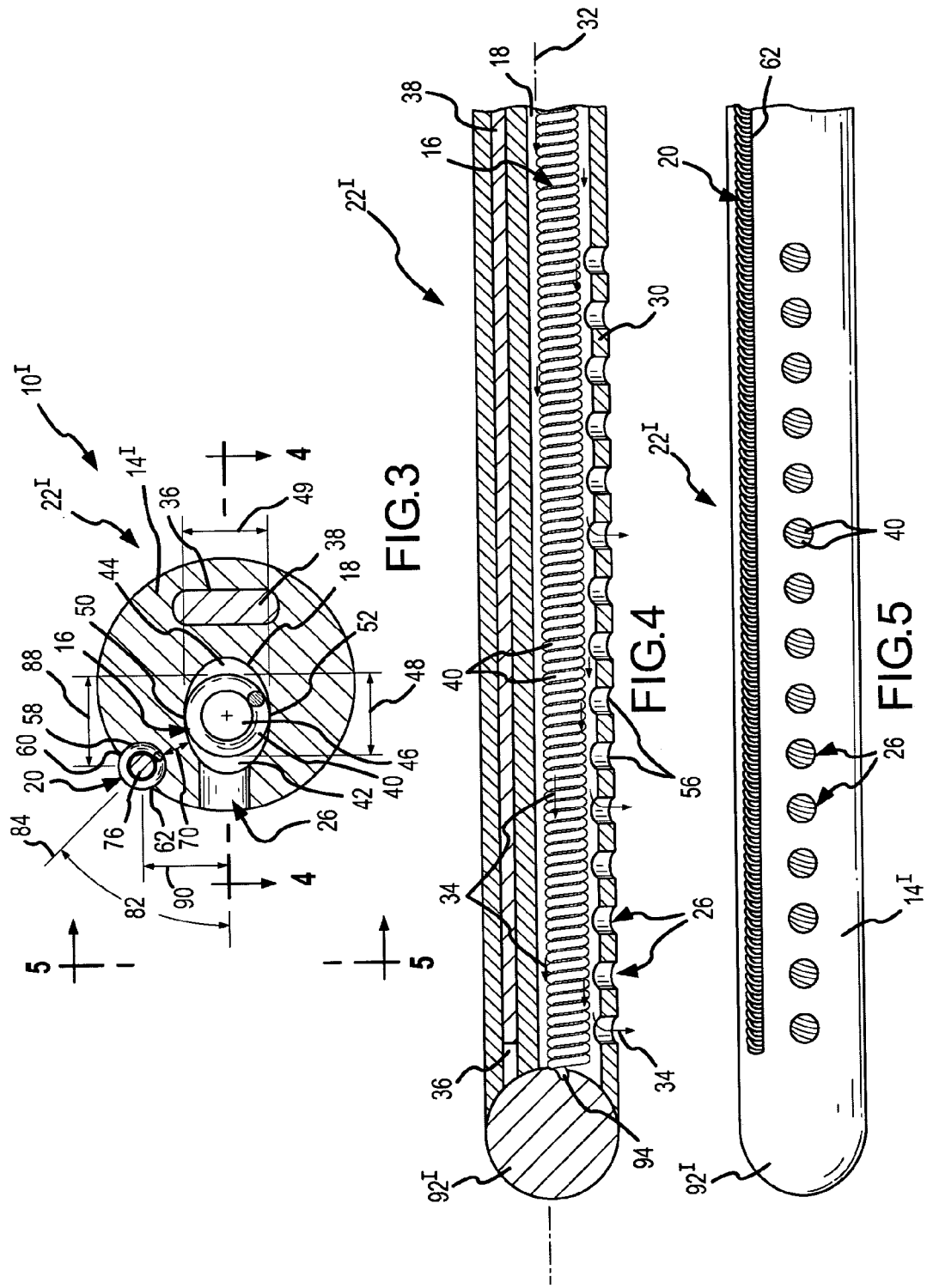

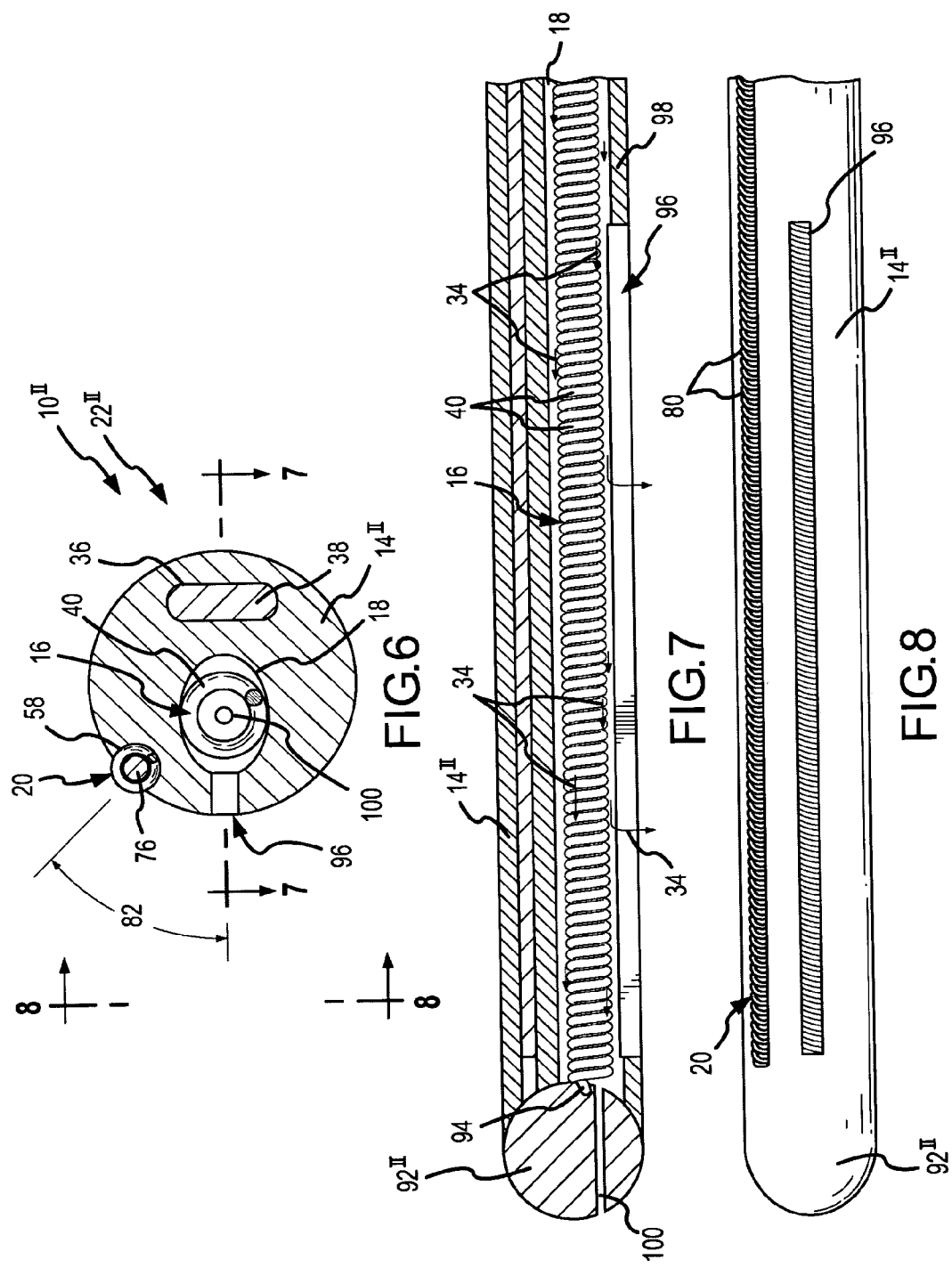

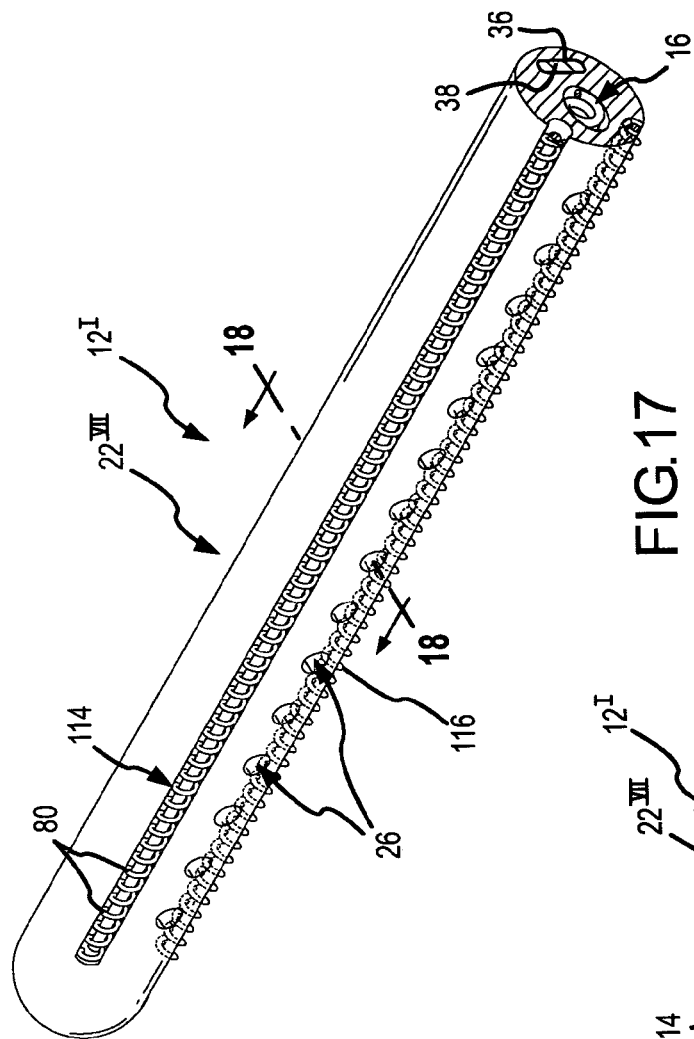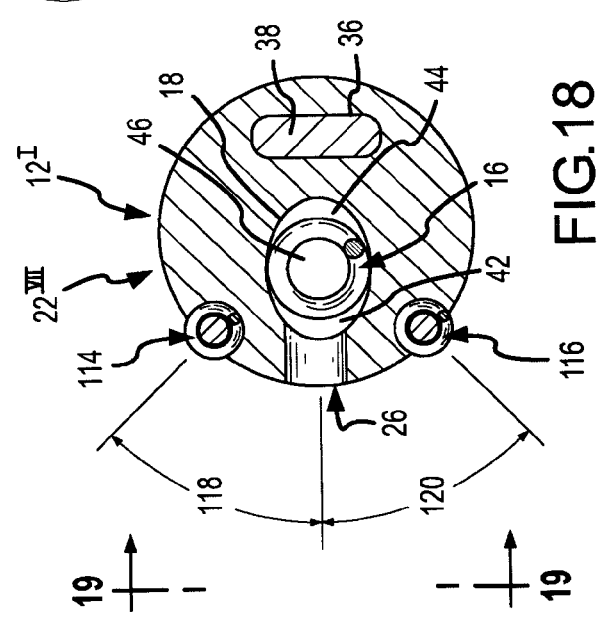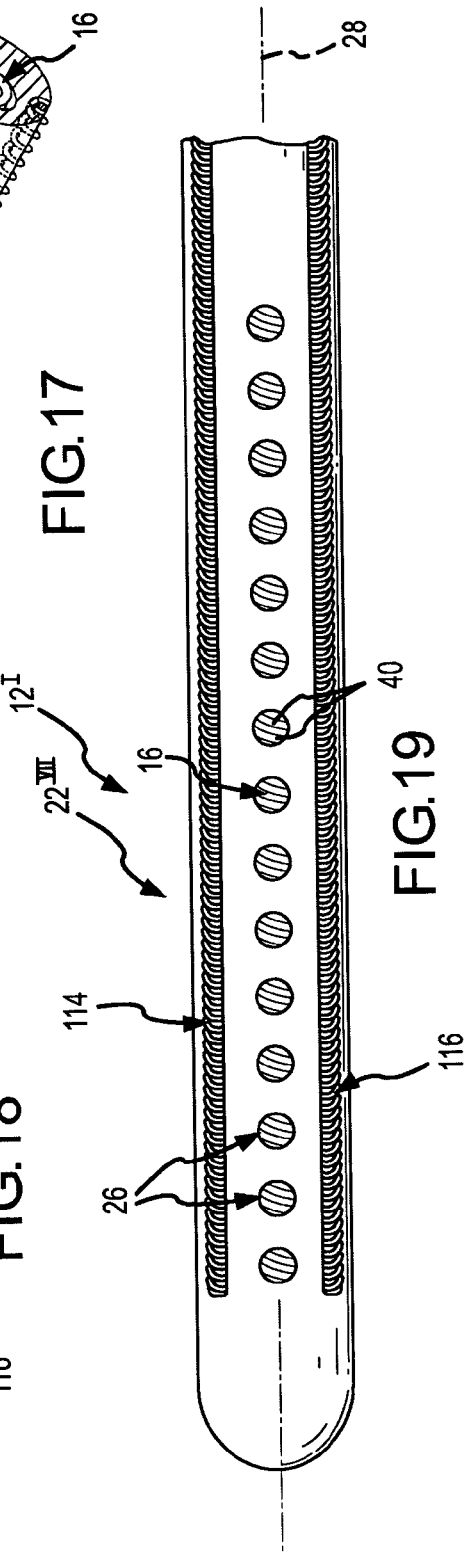

MULTIPOLAR, VIRTUAL-ELECTRODE CATHETER WITH AT LEAST ONE SURFACE ELECTRODE AND METHOD FOR ABLATION

BACKGROUND OF THE INVENTION a. Field of the Invention

The instant invention is directed toward virtual-electrode catheters and to methods for using such virtual-electrode catheters. More specifically, it relates to bipolar and multipolar, virtual-electrode catheters having at least one internal electrode and at least one surface electrode, and to methods of using these catheters for treatment of cardiac arrhythmias via, for example, radiofrequency (RF) ablation.

b. Background Art

Conventional catheter techniques of RF ablation for treating cardiac arrhythmias use RF electrodes in a unipolar mode. In this mode, only the active RF electrodes are placed at the site of the ablation. The dispersive electrodes are placed at locations remote from the ablation site, typically on the skin of the patient.

In the unipolar mode, the RF current decreases as $1/r^2$, and the RF energy decreases as $1/r^4$, where "r" is the radial distance from an active electrode of a catheter. Because tissue ablation is caused by RF energy deposition into the tissue, the depth of the ablation is limited to a narrow rim around the catheter electrode. Increased lesion depth, therefore, requires high power. High power, however, causes rapid temperature increases and potential "hot-spots" at the electrode-tissue interface.

The virtual electrode technique mitigates this problem of temperature increases at the electrode-tissue interface by using cooled conductive fluid flowing onto the tissue surface. The fluid flow rate necessary to provide adequate surface cooling depends upon the RF power being delivered. The higher the power, the higher the flow rate that is necessary. To create lesions 3-4 mm deep using existing devices may require 50 watts for 60 seconds and a fluid flow rate of 72 ml per minute. For a full-circumferential lesion, these same existing devices require a minimum of two separate procedures at these settings. The minimum RF energy delivered during the 120 seconds total duration is, therefore, 6000 Joules; and the total volume of fluid delivered is over 140 ml. By contrast, for a typical pulmonary vein of 22 mm diameter, a lesion size of 60 mm×3 mm×3 mm obtained with a temperature rise of 50° C. requires a total energy of only about 120 Joules. This means that only 2% of the applied RF energy is used to create the lesion. The remaining 98% of the applied energy is lost to heating other substances such as the infused fluid, the catheter body, surrounding tissue, blood, and other tissue fluids. Existing techniques can be, therefore, highly inefficient.

BRIEF SUMMARY OF THE INVENTION

It is desirable to be able to improve the efficiency of ablation, including RF ablation using virtual-electrode technology. Accordingly, it is an object of the disclosed invention to provide an improved ablation catheter and method for treatment of, for example, cardiac arrhythmias.

In one form, the present invention comprises a virtual-electrode catheter for treatment of tissue. The catheter comprises a catheter body with a sidewall and an outer surface; a first internal lumen extending within the catheter body and adapted to flowingly receive a conductive fluid; an exit feature comprising a flow path from the first internal lumen through the catheter body sidewall and the outer surface, the exit feature being adapted to permit the conductive fluid to exit from the first internal lumen toward the tissue; an internal flexible conductor mounted within the first internal lumen adjacent to the exit feature and an inner surface of the catheter body sidewall, wherein the internal flexible conductor is adapted to deliver treatment energy to the tissue via the conductive fluid in the first internal lumen; and at least one surface electrode mounted on the outer surface of the catheter body adjacent to the exit feature. The exit feature may be, for example, a plurality of exit portholes, at least one exit slot, or a plurality of micro-pores; and the exit feature may be symmetrically distributed about a porthole centerline extending longitudinally along the outer surface of the catheter body. The internal flexible conductor may be, for example, a coil electrode, a wire strand electrode, or a tubular electrode.

In another form, the invention comprises a virtual-electrode catheter for tissue ablation. In this form, the catheter comprises (a) a catheter body having an outer surface, an internal lumen, and a fluid exit feature extending between the internal lumen and the outer surface, wherein the exit feature is adapted to be placed against tissue, and wherein the internal lumen is adapted to deliver conductive fluid to the fluid exit feature; (b) an active internal electrode mounted within the internal lumen of the catheter body and adapted to contact the conductive fluid, wherein the active internal electrode is electrically connected to a source of ablative energy and is adapted to impart the ablative energy to the tissue via the conductive fluid; and (c) at least one passive external electrode mounted on the outer surface of the catheter body adjacent to the fluid exit feature, wherein the at least one passive external electrode is electrically connected to the source of ablative energy and is adapted to return at least a portion of the ablative energy to the source of ablative energy, whereby, upon activation of the source of ablative energy, an electric field is created between the active internal electrode and the at least one passive external electrode, and in the tissue adjacent to the fluid exit feature.

In yet another form, the present invention comprises a multipolar, virtual-electrode catheter for performing radiofrequency ablation of cardiac tissue. In particular, the catheter comprises (a) a catheter body defining an outer surface and an internal lumen, wherein the internal lumen is adapted to carry conductive fluid; (b) at least two metal electrodes positioned on the outer surface of the catheter body, wherein the metal electrodes are adapted for placement against the cardiac tissue; (c) a metal conductor positioned within the internal lumen and adapted to impart radiofrequency energy to the conductive fluid; (d) at least one opening on the outer surface of the catheter, the opening adapted to create a flow path for the conductive fluid in the internal lumen to flow out of the catheter and impinge upon the cardiac tissue as a virtual-electrode; and (e) at least one temperature sensor on the outer surface of the catheter body in close juxtaposition to the metal electrodes.

In another form, the present invention comprises a method for tissue ablation using a virtual-electrode catheter. In this form, the virtual-electrode catheter being used comprises (a) a catheter body with a sidewall and an outer surface; (b) a first internal lumen extending within the catheter body and adapted to flowingly receive a conductive fluid; (c) an exit feature comprising a flow path from the first internal lumen through the catheter body sidewall and the outer surface, the exit feature being adapted to permit the conductive fluid to exit from the first internal lumen toward the tissue; (d) an internal flexible conductor mounted within the first internal lumen adjacent to the exit feature and an inner surface of the catheter body sidewall, wherein the internal flexible conductor is adapted to deliver ablation energy to the tissue via the conductive fluid in the first internal lumen; and (e) at least one surface electrode mounted on the outer surface of the catheter body adjacent to the exit feature. The method according to this form of the invention comprises the steps of (a) flowing the conductive fluid within the first internal lumen and out of the exit feature; (b) delivering ablation energy to the internal flexible conductor; (c) generating an electric field between the internal flexible conductor and the at least one surface electrode; and (d) terminating delivery of the ablation energy upon creating of a lesion in the tissue.

In another form, the present invention comprises a method for tissue ablation using a virtual-electrode catheter. In particular, the method comprises the steps of (a) placing against the tissue both a first dispersive surface electrode and a second dispersive surface electrode, wherein the first and second surface electrodes are mounted on an outer surface of a catheter body of the virtual-electrode catheter; (b) flowing a conductive fluid trough a first internal lumen extending within the catheter body toward an exit feature that is adjacent to the first and second surface electrodes; (c) delivering ablation energy to an active internal flexible conductor within the first internal lumen; (d) generating a concentrated electric field between the internal flexible conductor and at least one of the first and second surface electrodes; and (e) terminating delivery of the ablation energy after creation of a lesion in the tissue.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 3 is a cross-sectional view taken along line 3-3 of FIG. 1.

FIG. 4 is a cross-sectional view taken along line 4-4 of FIG. 3.

FIG. 5 is a front elevation of the embodiment depicted in FIGS. 1-4 taken in the direction of line 5-5 of FIG. 3.

FIG. 6 is a cross-sectional view similar to FIG. 3, but depicts a bipolar, virtual-electrode catheter according to a second embodiment of the present invention.

FIG. 7 is similar to FIG. 4, but is a cross-sectional view of the bipolar, virtual-electrode catheter according to the second embodiment, taken along line 7-7 of FIG. 6.

FIG. 8 is similar to FIG. 5, but is a front elevation of the bipolar, virtual-electrode catheter according to the second embodiment, taken in the direction of line 8-8 of FIG. 6.

FIG. 17 is a fragmentary, isometric view of a multipolar, virtual-electrode catheter according to a seventh embodiment of the present invention.

FIG. 18 is a cross-sectional view of the multipolar, virtual-electrode catheter according to the seventh embodiment of the present invention, taken along line 18-18 of FIG. 17.

FIG. 19 is a fragmentary, front elevation of the multipolar, virtual-electrode catheter according to the seventh embodiment of the present invention, taken in the direction of line 19-19 of FIG. 18.

DETAILED DESCRIPTION OF THE INVENTION

Several embodiments of a virtual-electrode catheter according to the present invention are disclosed, including embodiments of a bipolar, virtual-electrode catheter (e.g., $10'$ in FIG. 1) and embodiments of a multipolar, virtual-electrode catheter (e.g., $12'$ in FIG. 17). In general, these virtual-electrode catheters comprise a catheter body (e.g., $14'$ in FIG. 1) with an internal flexible current carrier or electrode (e.g., 16 in FIG. 1) mounted in an internal lumen (e.g., 18 in FIG. 1), and at least one surface electrode (e.g., 20 in FIG. 1). Details of the various embodiments of the present invention are described below with specific reference to the figures.

Figure 1:
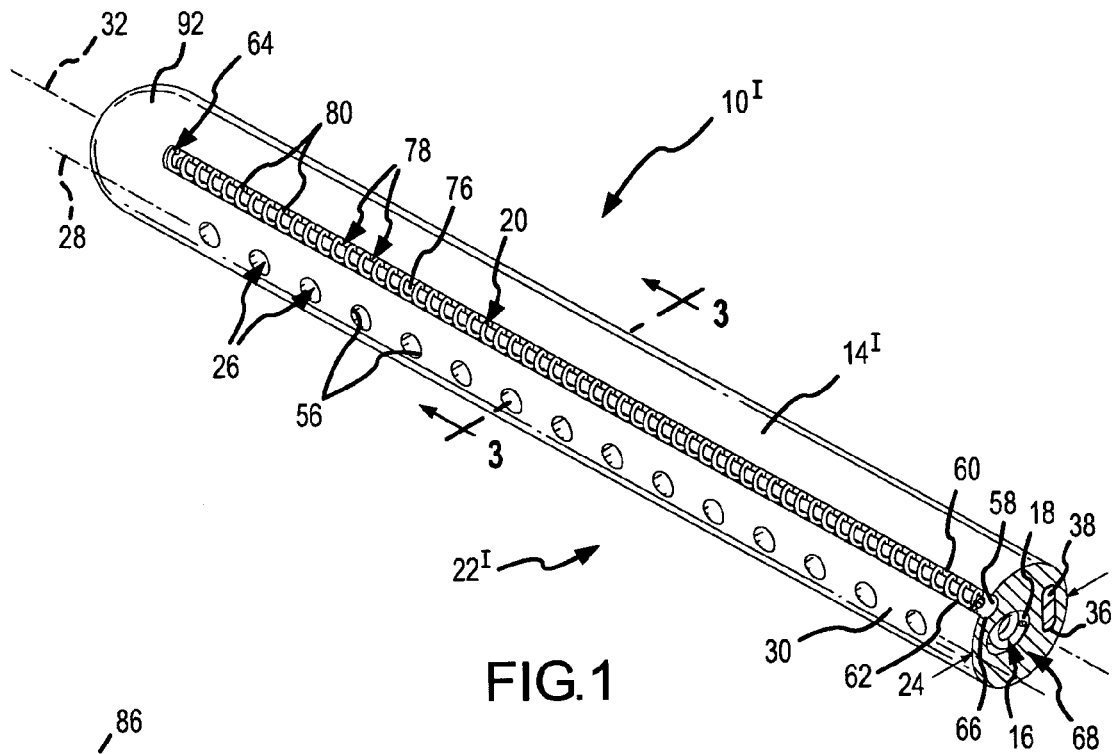
FIG. 1 is a fragmentary, isometric view of a bipolar, virtual-electrode catheter according to a first embodiment of the present invention.

FIGS. 1-5 depict a distal portion 221 of a bipolar, virtual-electrode catheter $10'$ according to a first embodiment of the present invention. The catheter comprises a catheter body 14'. As shown in FIG. 1, in this first embodiment of the bipolar, virtual-electrode catheter 10', the catheter body 14' has a circular cross section that is relatively small. For example, the catheter body 14' may have a diameter 24 of 0.091 inches (approximately 2.31 mm). Clearly, this particular diameter for the catheter body 14' is not required; and the bipolar, virtual-electrode catheter 10' according to the present invention may be sized as required to fit, for example, specific vascular or other body cavities.

As shown in FIGS. 1, 2, 4, and 5, an exit feature extends through a sidewall 30 of the catheter body 14'. In particular, the exit feature in this first embodiment comprises a plurality of exit portholes or nozzles 26 that are arranged along a longitudinally-extending porthole centerline 28 along the surface of the catheter body 14'. As best seen by looking at FIGS. 3 and 4, these exit portholes 26 extend through the sidewall 30 of the catheter body 14'. In the depicted embodiment, as shown to good advantage in FIGS. 3 and 4, the exit portholes 26 extend radially through the sidewall 30 relative to a catheter longitudinal axis 32.

The catheter body 14' includes at least one longitudinally-extending internal lumen 18 in which an internal flexible current carrier or conductor 16 is mounted. If desirable, more than one elliptical internal lumen may be present. In the embodiment depicted in FIGS. 1-5, the internal lumen 18 has an elliptical cross section, which, among other advantages mentioned below, helps direct fluid 34 toward the exit portholes 26, but the internal lumen need not have an elliptical cross section. The elliptical cross sectional configuration efficiently moves a high volume of fluid 34 in a more compact configuration. The catheter body of this embodiment also comprises an optional, second lumen 36 in which a shape-retention or shape-creating rail or wire 38 is mounted (e.g., a nickel-titanium wire, which is also know as NiTi or Nitinol wire). This rail or wire 38 helps with steering and shaping the distal portion 22' of the catheter 10'.

Figure 2:
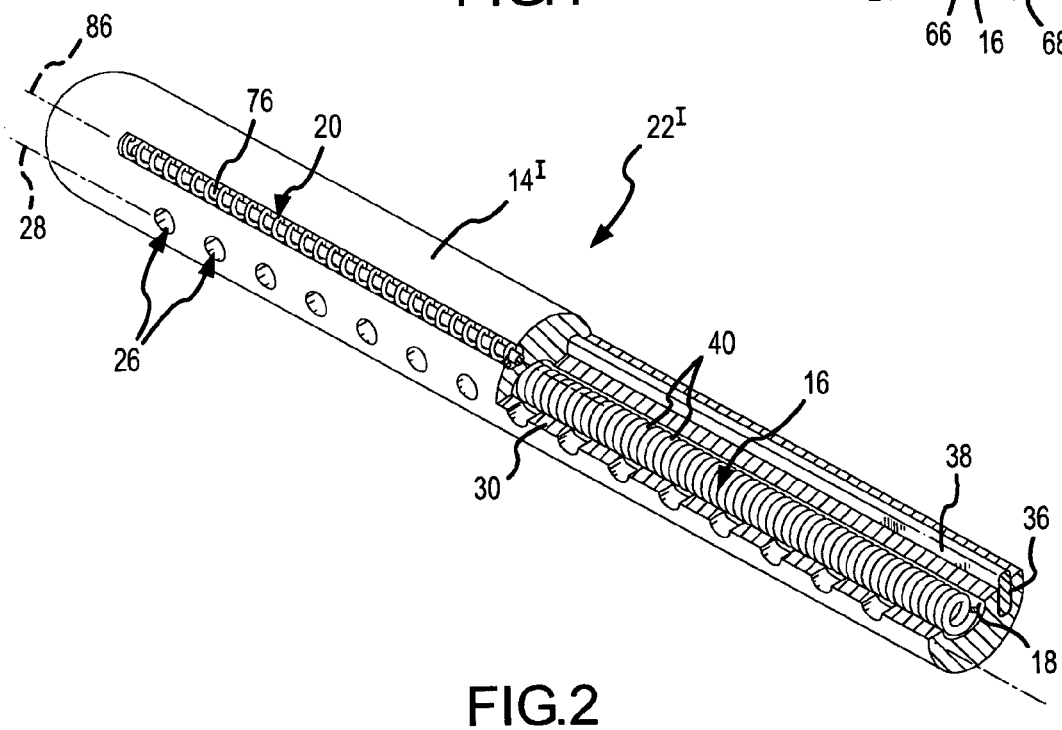
FIG. 2 is a fragmentary, isometric view similar to FIG. 1, but depicts a portion of the catheter body broken-away to reveal various internal features of the first embodiment of the present invention.

In this first embodiment of the present invention, the internal flexible electrode 16 comprises a single, large, internal coil electrode. As shown in FIG. 2, desirably this internal coil electrode 16 has a tight spring pitch (i.e., tightly wound coils 40) with individual coils 40 that are closely packed (e.g., 2-3 turns between adjacent portholes 26 or approximately 1/1000th of an inch between coils). The individual coils or turns 40 of the large internal coil electrode permit fluid 34 flowing through the elliptical internal lumen 18 to pass between the coils or turns comprising the electrode before exiting from the catheter 10' via the exit portholes 26. These tightly wound coils 40 help regulate fluid flow within the internal lumen 18 of the catheter body 14' and out of the exit portholes 26. In FIG. 5, the individual turns 40 of the larger internal coil 16 are visible through the exit portholes 26. The large internal coil stretches and relaxes and is put under tension and compression as the distal portion 22' of the bipolar, virtual-electrode catheter 10' is manipulated during use of the device. As the coil thus flexes, the gaps between adjacent coils may change in size slightly. This may create some pressure gradients in the flow distribution along the plurality of exit portholes, which may affect the impedance and heating of the conductive fluid 34 (i.e., the cooling fluid) flowing in the internal lumen 18 of the catheter 10'.

Since the internal flexible electrode 16 depicted in the embodiment of FIGS. 1-5, is a large coil having an annular cross-section, when this large coil is mounted in the elliptical internal lumen, a flow channel comprising a forward crescent-moon-shaped region 42, a rearward crescent-moon-shaped region 44, and a circular central region 46 (in cross section) are defined (see FIG. 3). In particular, the large coil electrode 16 is sized such that its outside diameter 48 is approximately the same length as the length of the minor axis 49 of the elliptical cross-section of the internal lumen 18. Thus, the large coil electrode 16 extends from the top 50 to the bottom 52 of the elliptical internal lumen (FIG. 3), across the internal lumen's minor axis 49. In this particular configuration, the large internal coil's position relative to the elliptical internal lumen, and thus relative to the exit portholes or nozzles 26, remains relatively unchanged even when the distal portion 22' of the bipolar, virtual-electrode catheter 10' is bent or curved during manipulation of the catheter during use. In other words, although the distal portion of the bipolar, virtual-electrode catheter depicted in all of the figures is shown as straight for simplicity, the catheter may be pre-curved for a particular application and/or the catheter may be curveable or shapeable during use by manipulation of, for example, the rail 38 visible in, for example, FIGS. 1-4. Nevertheless, in this depicted embodiment, the large coil electrode 16 remains relatively fixed within the internal lumen 18.

The internal flexible electrode may alternatively comprise a flexible solid wire (not shown) rather than a coil. This type of internal flexible electrode may, however, have a few drawbacks. For example, if the internal flexible electrode comprises a solid wire having a annular cross section, and if that annular cross section has an outer diameter equal to the length of the minor axis of the internal lumen's elliptical cross section, any fluid flowing in the rearward crescent-moon-shaped region or flow channel 44 would be inhibited or prohibited from reaching the exit portholes 26. On the other hand, if the internal flexible electrode comprises a wire of a diameter that does not match the length of the minor axis of the internal lumen's elliptical cross section, the wire may shift relative to the exit portholes 26 during manipulation of the bipolar, virtual-electrode catheter 10'. For example, bending the catheter to form a curve may place part of the wire closer to some of the exit portholes than others, which may undesirably alter the virtual-electrode effects longitudinally along the distal portion 22' of the bipolar, virtual-electrode catheter 10'. In other words, this shifting can lead to undesirable variations and concomitant unpredictability in the energy delivered via the virtual-electrode catheter during use.

As alluded to above, a shape-retention or shape-forming rail or wire 38 (e.g., a NiTi wire) may be present. In particular, as shown in FIGS. 1-4, the catheter body 14' may comprise the second lumen 36, which extends longitudinally through the catheter body and accommodates this wire or rail 38. In the depicted embodiment, the wire or rail has a rounded-rectangular cross-sectional configuration that is "keyed" to, or that complements, the cross-sectional configuration of the second lumen 36 (see FIGS. 1-4). When present, this wire or rail 38 can perform different functions. For example, the wire or rail may be "biased or preset" to take a desired curvature. In particular, the wire or rail may be preset to force the distal portion 22' of the bipolar, virtual-electrode catheter into a particular curvature. Thus, once the catheter has been delivered adjacent to tissue 54 (see FIG. 24) to be diagnosed or treated using an introducer or other catheter (not shown), the distal portion 22' of the catheter is extended past the distal end of the introducer or other catheter that delivered the virtual-electrode catheter 10' to the tissue to be treated. Once the bipolar, virtual-electrode catheter is extended out of the delivery device, the wire or rail 38 would cause the distal portion 22' of the bipolar, virtual-electrode catheter to assume the desired configuration. In this manner, an ultimately curved distal portion may be delivered to a treatment or diagnosis site prior to taking its curved configuration. Alternatively, the wire or rail may be connected to some type of control handle or other device (not shown) that remains external to a-patient, whereby manipulation of this control handle or other device allows a physician to manipulate the shape and placement of the distal portion of the catheter.

As shown to best advantage in FIG. 4, conductive fluid 34 or suspension flows substantially longitudinally through the elliptical internal lumen 18, along and around the large internal coil 16. As used herein, "suspension" means a mixture that may comprise particles, fluids, or other materials added to a base fluid to adjust the electrical or other properties of the base fluid. Eventually, the conductive fluid or suspension 34 is delivered to the tissue 54 (see FIGS. 24-26) to be treated. As explained further below, during an ablation procedure, that tissue would be adjacent to the outside surface of the distal portion of the bipolar, virtual-electrode catheter, adjacent to the outer edges 56 of the exit portholes. The large internal coil 16 thus is able to deliver energy (e.g., RF energy) to the tissue 54.

Since the present invention preferably operates in a bipolar or multipolar mode, the device further comprises at least one surface electrode 20 in addition to the internal flexible electrode 20. In the first embodiment of the present invention, which is depicted in FIGS. 1-5, the surface electrode comprises a single coil of conductive material (e.g., metal, conductive silicon, or conductive polymer), which may be seen in FIGS. 1, 2, 3, and 5. The coil may be hollow (i.e., the wire wound into the coil may be a hollow-core or tubular wire). In the embodiment depicted in these figures, the surface coil electrode 20 is mounted in a longitudinally-extending, C-shaped channel 58 on the surface of the distal portion $22^I$ of the bipolar, virtual-electrode catheter. As shown to good advantage in FIGS. 1 and 3, this longitudinally-extending channel 58 has a C-shaped cross section in this embodiment, wherein a top edge 60 and a bottom edge 62 of the "C" retain the surface electrode 20 in the channel 58. The surface electrode 20, in this embodiment, may be mounted in the channel 58 by, for example, inserting a longitudinal end 64 of the surface electrode 20 into the channel starting from an end of the C-shaped channel 58.

For example, if, in the embodiment as depicted in FIG. 1, the C-shaped channel terminates at point 66, the surface electrode 20 could be inserted into the C-shaped channel 58 from right to left in the drawing of FIG. 1. Subsequently, the distal portion $22^I$ may be mounted (e.g., by adhesion) to a section of catheter shaft (not shown) by adhering the surface 68 depicted in FIG. 1 to a complementary surface on a distal end of the portion of catheter shaft (not shown) that will be used to manipulate the distal portion $22^I$ of the bipolar, virtual-electrode catheter $10^I$ into position.

The elliptical lumen 18 makes it possible for the width of material 70 (FIG. 3) between the C-shaped channel 58 and the elliptical internal lumen 18 to be larger than it could be if the internal lumen had a circular cross section. This is advantageous since it facilitates better heat dissipation, particularly when the surface electrode 20 and/or the internal electrode 16 heat during use of the catheter $10^I$ for an ablation procedure.

As explained further below, in the first embodiment of the present invention (FIGS. 1-5), the large internal coil 16 acts as the active electrode. Thus, the large internal coil would be connected to, for example, an RF current source (not shown) outside of the patient's body via one or more conductors extending longitudinally through the catheter shaft to a proximal portion of the catheter shaft that remains outside of the patient's body. The small coil surface electrode 20 serves a dispersive electrode when the catheter $10^I$ is used in a bipolar mode, and would be connected to the return end of the RF source in this mode. The surface electrode coil 20 thus acts as an inactive return electrode. In other words, during operation of the catheter according to the present invention in its bipolar mode, RF energy (or some other type of energy) may be delivered to the large internal coil 16, and then exit from the exit portholes 26 via conductive fluid 34 flowing through and around the large internal coil 16 (FIG. 4). This RF energy is then "captured" or returned by the surface electrode coil 20 to the RF generator or ground, which creates an electric field 72 (FIG. 24) between the large internal coil 16 and the surface electrode coil 20 in the tissue 54 adjacent to the exit portholes 26 and the surface electrode coil 20.

When the first embodiment, which is depicted in FIGS. 1-5, is operated in a first mode, the RF energy exits the internal lumen 18 via the exit portholes 26 before traveling to the surface electrode 20. The exit portholes are thus sized and spaced appropriately (see, for example, US patent application publication no. US 2004/0143253 A1, which is hereby incorporated by reference as though fully set forth herein). The exit portholes 26, which are distributed along the porthole centerline 28, are configured to create "nozzle effects" with minimum pressure loss. If the exit portholes or nozzles 26 are too large, an inordinate or undesirable amount of conductive fluid 34 may be delivered to the patient's bloodstream 74 (FIG. 24) and the electric field that is desirably established in the tissue may be "washed away." If, on the other hand, the exit portholes 26 are too small, electrical resistance may exceed desirable levels, making it difficult to deliver the desired amount of ablation energy to the tissue to be treated.

A thermal sensor 76 may be mounted adjacent to the surface electrode 20. In the particular embodiment depicted in FIGS. 1-5, for example, a longitudinally-extending thermal sensor 76 extends within the surface electrode coil 20. This thermal sensor may be any type of temperature sensor (e.g., a thermocouple, a thermister, or a fiber optic sensor). Since, in this embodiment, the surface electrode 20 is not actively cooled, having a thermal sensor placed in close juxtaposition to the external, surface electrode, makes it possible to monitor when the surface electrode may be approaching undesirably high temperatures. If the surface electrode were to become too hot, coagulum may be formed in the gaps 78 between the individual coils 80 of the surface electrode causing performance degradation and possibly other complications. As previously mentioned, the surface electrode coil 20 may be formed from a hollow wire. If the surface electrode coil were constructed from such a hollow wire, a cooling fluid may be pumped through the hollow wire to help regulate the temperature of the surface electrode.

Desirably, the surface area of the surface electrode is selected so that the surface electrode 20 can handle the energy being delivered to it by the internal coil electrode 16 via the conductive saline 34. Also, the surface area of the surface electrode may be configured so that energy may be delivered in reverse, that is, from the surface electrode 20 to the internal coil electrode 16.

Referring most specifically to FIG. 3, the radial offset angle 82 of the surface electrode 20 relative to the exit portholes 26 is another consideration. By placing the active electrode 16 and the dispersive electrode 26 sufficiently close to each other, it is possible to provide high current density and a highly-localized electric field 72 within the tissue 54 (see FIGS. 24-26) contacting the distal portion $22^I$ of the bipolar, virtual-electrode catheter $10^I$ adjacent to the exit portholes 26 and adjacent to the surface electrode 20. The offset angle 82 (see FIG. 3) between the centerline 28 (see FIG. 2) of the exit portholes 26 and the radial line 84 (see FIG. 3) passing through the longitudinally-extending axis 86 (see FIG. 2) of the surface electrode (i.e., the angular displacement of the longitudinal centerline of the surface electrode relative to the longitudinal centerline of the exit portholes) may be, for example, 45°. In one example, wherein the bipolar, virtual-electrode catheter has the circular cross section depicted in FIGS. 1-3, and the diameter 24 (FIG. 1) of that circular cross section is approximately 0.091 inches (i.e., approximately 2.31 mm), the outside diameter 48 of the large internal coil 16 may be 0.024 inches (i.e., approximately 0.61 mm), and the center of the surface electrode coil may be offset forward of the rear edge of the internal coil 16 by a distance 88 of approximately 0.029 inches (i.e., approximately 0.74 mm), and the surface electrode coil centerline may be displaced a distance 90 of approximately 0.029 inches above the centerline 28 of the exit portholes 26.

If the offset angle 82 is too small or acute, no energy (or an undesirably low amount of current) may pass through the tissue 54 (see, e.g., FIG. 24), and the energy may predominately pass directly from the exit portholes 26 to the surface electrode 20, with an undesirably small amount of energy passing through the tissue 54. Alternatively, if the offset angle 82 is too large, the electric field 72 may become undesirably attenuated. In this latter case, the bipolar, virtual-electrode catheter $10^I$ effectively acts as a unipolar, virtual-electrode catheter.

As shown to good advantage in FIG. 4, the distal portion $22^I$ of the bipolar, virtual-electrode catheter $10^I$ may comprise a terminal sphere or ball $92^I$ at its distal extremity. This terminal sphere, which may be solid or hollow, may also be used to stabilize the internal electrode 16. In the depicted embodiment, for example, the large internal coil 16 includes a distal projection or anchor 94. This distal projection 94 can comprise a short section at the extreme distal end of the large internal coil 16 that is mounted in or otherwise affixed to the terminal sphere $92^I$. The anchored distal projection 94 helps keep the large internal coil from floating or shifting around undesirably and, thus, helps to ensure that the large internal coil extends over all of the exit portholes.

FIGS. 6-8 depict various views of a distal portion $22^{II}$ of a bipolar, virtual-electrode catheter $10^{II}$ according to a second embodiment of the present invention. This second embodiment is similar to the first embodiment. The exit feature, however, is an exit slot 96 that extends longitudinally along and through an external wall 98 of the catheter body $14^{II}$ and into the elliptical internal lumen 18, rather than the exit portholes 26 of the first embodiment. In this second embodiment, a single large internal coil 16 is again present and the surface electrode 20 is again depicted as a single coil. Also visible in FIGS. 6 and 7, is a through port or release hole 100. This release hole, although only shown in FIGS. 6 and 7, may be combined with any of the embodiments disclosed herein. This release hole 100 is a small hole or pathway extending from the elliptical internal lumen 18 to the outside of the bipolar, virtual-electrode catheter $10^{II}$. In the embodiment depicted in FIGS. 6-8, if the distal portion of the slot 96 were to become blocked by the tissue, for example, the through port 100 would help avoid the formation of a stagnation pool adjacent to the terminal sphere $92^{II}$ since the saline or other conductive fluid 34 that is expected to exit the elliptical internal lumen 18 at the distal end of the slot 96 could exit the catheter via the through port 100.

It is possible that, if the anchored distal projection 94 were not present, the large internal coil 16 may not extend over the entire set of exit portholes 26 (first embodiment) or over the entire length of the exit slot 96 (second embodiment). If the large internal coil 16 were not present over one or more of the exit portholes 26, for example, the saline or other conductive fluid 34 being flushed around, along, and within the large internal coil may get too hot during use. In particular, as the conductive fluid moves around, along, and within the large internal coil, energy traveling through that coil 16 is delivered to the conductive fluid 34 for ultimate delivery through the exit portholes 26 (or slot 96) to the dispersive electrode (i.e., the surface electrode 20 visible in FIGS. 1-3, 5, 6, and 8). This energy delivery causes heating of the conductive fluid 34, which, in addition to carrying energy, also serves a cooling function. If the large internal coil 16 does not extend over a couple of portholes 26, for instance, a disproportionately high percentage of the cooling fluid may exit from these "uncovered" and thus unrestricted portholes. This would potentially starve the remaining portholes of cooling fluid, resulting in potential heat build-up at these "covered" and thus restricted portholes, possibly leading to increased coagulum formation at the portholes experiencing reduced flow.

Similarly, if the large internal coil 16 were to shift proximally and thus no longer extend over the distal portion of the slot 96, for example, the flow of the saline or other conductive fluid 34 through this portion of the slot may increase, thereby "starving" the remainder of the slot of cooling fluid, leading to possible increases in coagulum formation along the portion of the slot experiencing reduced flow of cooling fluid. By anchoring the distal end of the large internal coil 16 to the terminal sphere $92^I$, $92^{II}$, these unexpected and undesirable variations in the volume of fluid flowing through different portions of the slot 96 or through different exit portholes 26 can be better controlled. If the most distal portholes or the most distal portion of the slot were to become blocked, it would become increasingly difficult to get uniform flow from the remaining portholes or the remaining portion of the slot since the saline flowing in the elliptical internal lumen may then be flowing at a rate that is no longer correctly tailored to the total area of the "exit opportunities."

Figure 9:
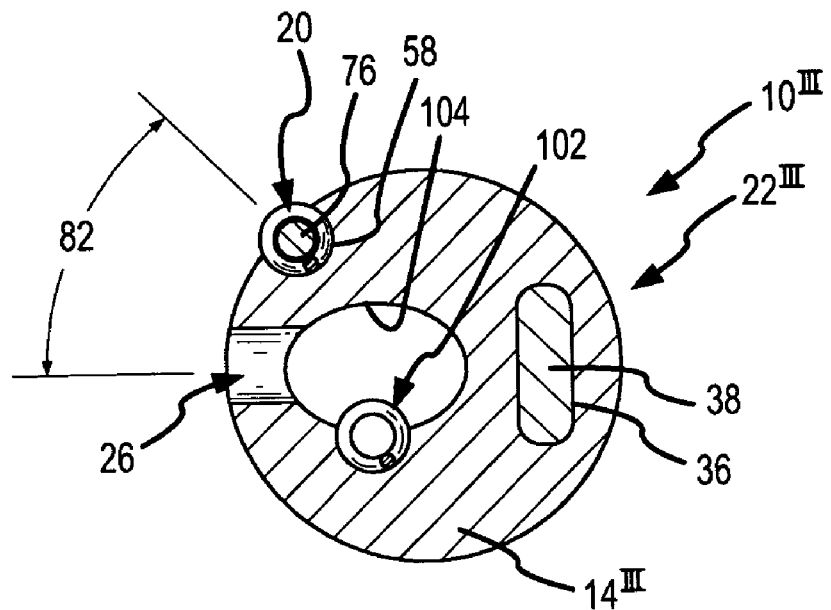
FIG. 9 is similar to FIGS. 3 and 6, but depicts a cross-sectional view of a bipolar, virtual-electrode catheter according to a third embodiment of the present invention.

FIG. 9 is similar to FIGS. 3 and 6, but depicts a cross-sectional view of a distal portion $22^{III}$ of a bipolar, virtual-electrode catheter $10^{III}$ according to a third embodiment of the present invention. The third embodiment $10^{III}$ is most similar to the first embodiment $10^I$. In the third embodiment, however, the single large internal coil electrode 16 has been replaced by a single small internal coil electrode 102. In other words, in the embodiment depicted in FIG. 9, the internal flexible current carrier or electrode is a single small coil electrode 102 that is partially embedded in a sidewall of the internal lumen 104. This single small internal electrode 102 accommodates, for example, a higher flow volume of conductive fluid 34 through the elliptical internal lumen 104 since the internal lumen 104 has less of its cross-sectional area obscured or blocked by the internal flexible electrode 102. The catheter body $14^{III}$ depicted in FIG. 9 again includes the optional wire or rail 38 for shaping or steering the distal portion $22^{III}$ of the virtual-electrode catheter $10^{III}$. This second lumen 36 and the wire or rail 38 need not be present.

Figure 10:
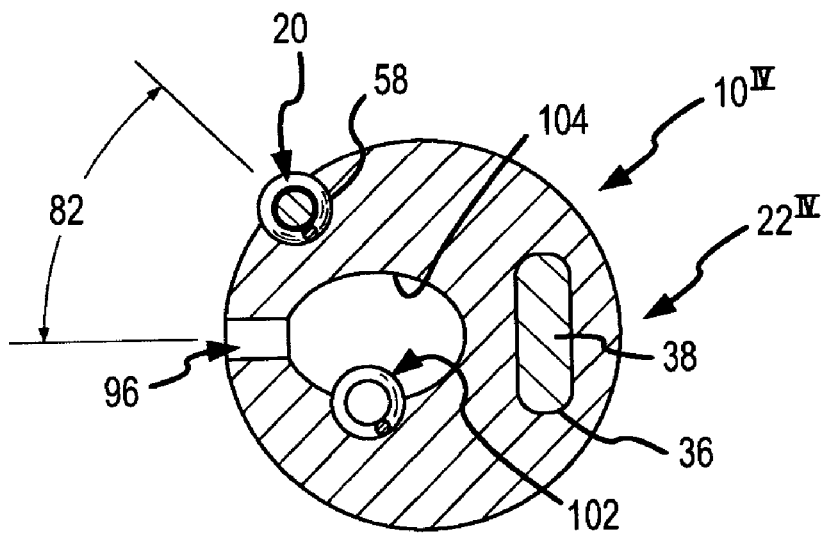
FIG. 10 is similar to FIGS. 3, 6, and 9, but depicts a cross-sectional view of a bipolar, virtual-electrode catheter according to a fourth embodiment of the present invention.

FIG. 10 is a cross-sectional view similar to FIGS. 3, 6, and 9, but depicts a distal portion $22^{IV}$ of a fourth embodiment $10^{IV}$ of the present invention. The fourth embodiment $10^{IV}$ is most similar to the second embodiment $10^{II}$, but the large internal coil 16 has again been replaced by a small internal coil 102. This fourth embodiment comprises an exit slot 96 like the exit slot depicted in the embodiment of FIGS. 6-8.

Figure 11:
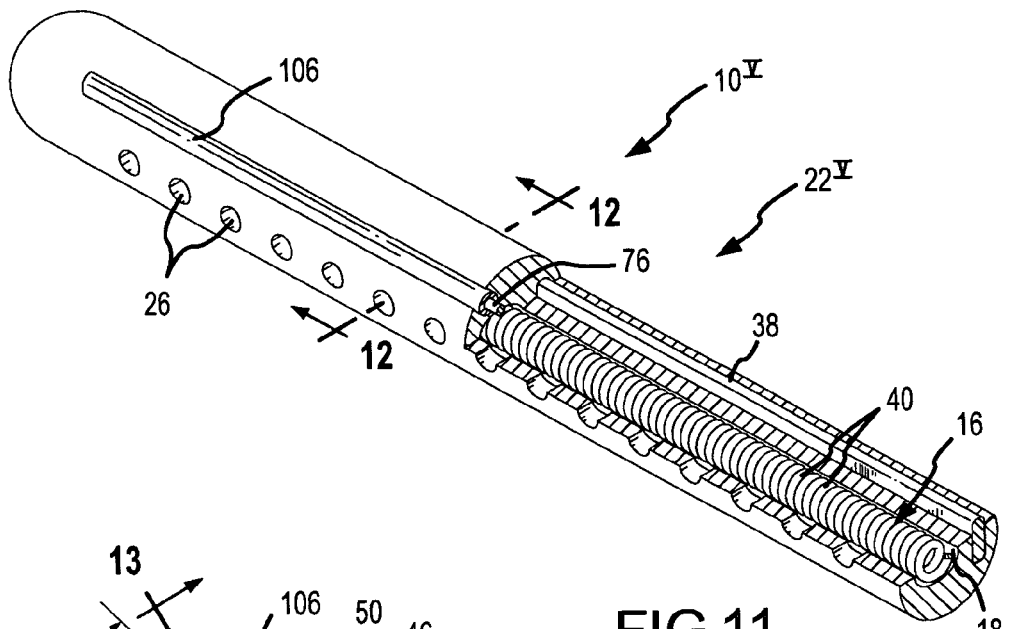
FIG. 11 is similar to FIG. 2, but depicts a fragmentary, isometric view of a bipolar, virtual-electrode catheter according to a fifth embodiment of the present invention, with a portion of the catheter body broken-away to reveal various internal features.
Figure 12:
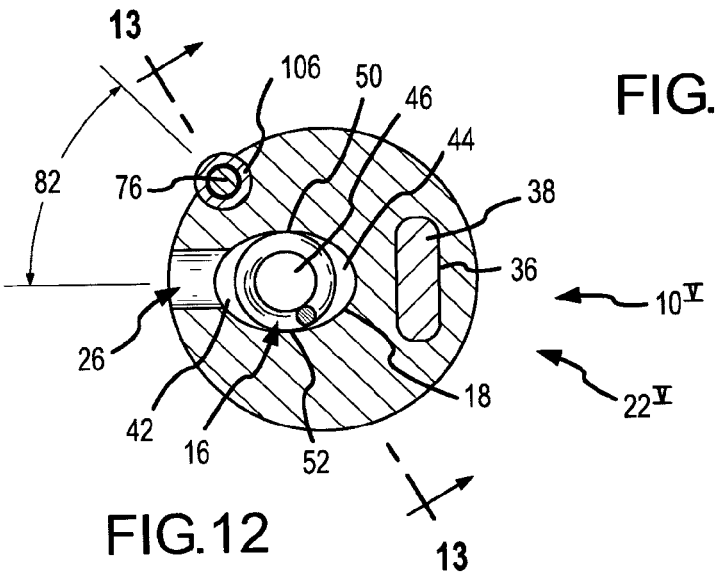
FIG. 12 is a cross-sectional view of the bipolar, virtual-electrode catheter according to the fifth embodiment of the present invention, taken along line 12-12 of FIG. 11.
Figure 13:
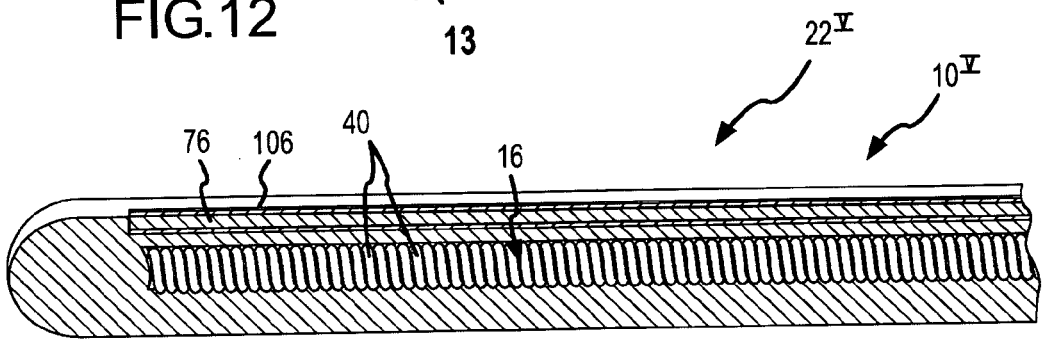
FIG. 13 is a fragmentary, cross-sectional view of the bipolar, virtual-electrode catheter according to the fifth embodiment of the present invention, taken along line 13-13 of FIG. 12.

FIGS. 11-13 depict a distal portion $22^V$ of a bipolar, virtual-electrode catheter $10^V$ according to a fifth embodiment of the present invention. FIG. 11 is similar to FIG. 1. In the fifth embodiment $10^V$, however, the surface electrode is a thermally and electrically conductive tube 106 rather than a coil 20 (FIG. 1). This surface electrode tube 106 may be metal, or may be constructed from some other conductive material (e.g., conductive silicone carbide or conductive polymer). For example, the surface electrode tube 106 depicted in FIGS. 11-13 may be a NiTi metal tube, potentially having shape memory characteristics. The surface electrode tube 106 may, accordingly, provide some force that helps shape the distal portion $22^V$ of the bipolar, virtual-electrode catheter $10^V$ as the catheter is placed adjacent to the tissue 54 to be treated.

In the fifth embodiment $10^V$, a thermal sensor 76 is inserted into the center or core of the surface electrode tube 106. Since the surface electrode tube in this embodiment is not cooled, being able to monitor the temperature of the surface electrode tube via the thermal sensor allows the user an opportunity to prevent overheating of this electrode tube during use. In the embodiments depicted in FIGS. 1-10, each of which comprises a surface electrode coil 20, blood may become caught or trapped in the gaps 78 between the individual turns 80 of the surface electrode coil 20. Thus, it is possible that this blood in the gaps between adjacent coils of the surface electrode coil may become excessively heated during use of the virtual-electrode catheter to the point of forming coagulum. The surface electrode tube 106 of the fifth embodiment $10^V$ may alleviate some of these potential coagulation issues that may be present with a surface electrode coil 20.

FIG. 12 is a cross-sectional view taken along 12-12 of FIG. 11. This figure again shows the surface electrode tube 106. As shown in FIGS. 11-13, the surface electrode tube is completely filled by the thermal sensor 76. In an alternative form, however, the thermal sensor may not completely fill the internal volume of the surface electrode tube, or the thermal sensor may be completely absent from the inside of the electrode tube 106. In either of these latter alternative configurations, a cooling fluid may be present inside of (possibly flowing within) the surface electrode tube 106. For example, the surface electrode tube may carry room temperature saline to provide some cooling and heat dissipation as the surface electrode tube performs its function of a dispersive electrode and receives energy from the internal flexible electrode (e.g., the large internal coil 16 depicted in FIGS. 11-13).

FIG. 13 is a fragmentary, cross-sectional view taken along line 13-13 of FIG. 12. As shown in this figure, the outer diameter of the large internal coil 16 may be selected in order to substantially, if not completely, bridge the distance between the top 50 and bottom 52 of the elliptical internal lumen 18. In other words, the outer diameter of the large internal coil may be substantially the same as the length of the minor axis of the elliptical cross section of the internal lumen. Since line 13-13 of FIG. 12 slices through the distal portion $22^V$ of the virtual-electrode catheter $10^V$ adjacent to the points where the outer surface of the large internal coil 16 contacts the inner surface of the elliptical internal lumen 18, the large internal coil 16 is depicted in FIG. 13 as substantially filling the elliptical internal lumen. The forward and rearward crescent-moon-shaped flow channels 42,44 would, however, remain present in the configuration depicted in FIGS. 11-13.

Figure 14:
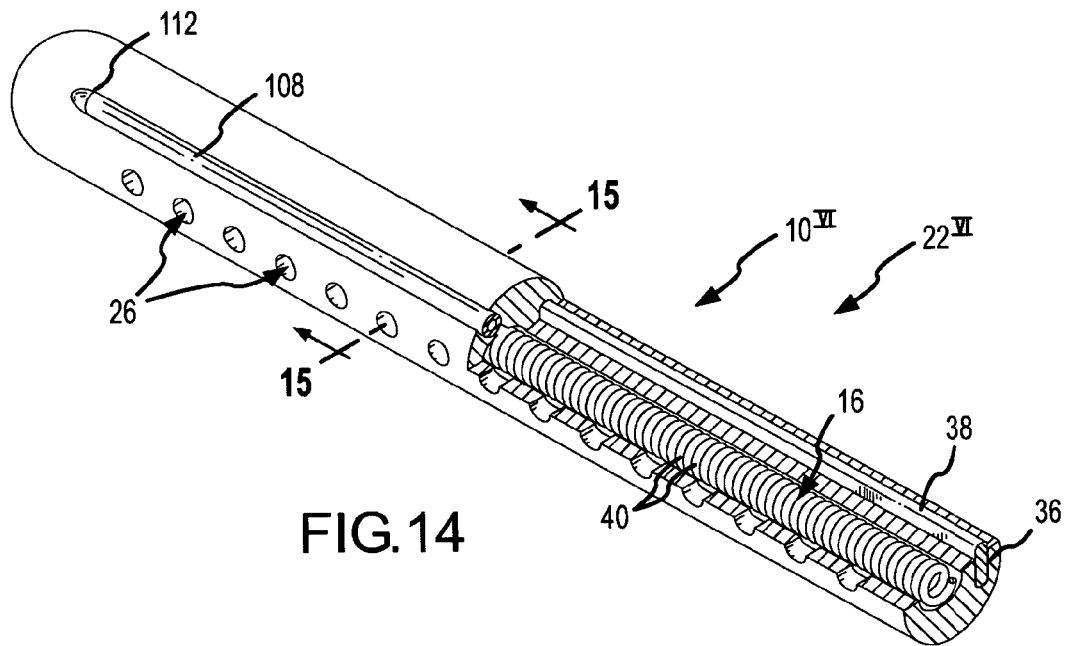
FIG. 14 is similar to FIG. 11, but is a fragmentary, isometric view of a bipolar, virtual-electrode catheter according to a sixth embodiment of the present invention with a portion of the catheter body broken-away to reveal various internal features.
Figure 15:
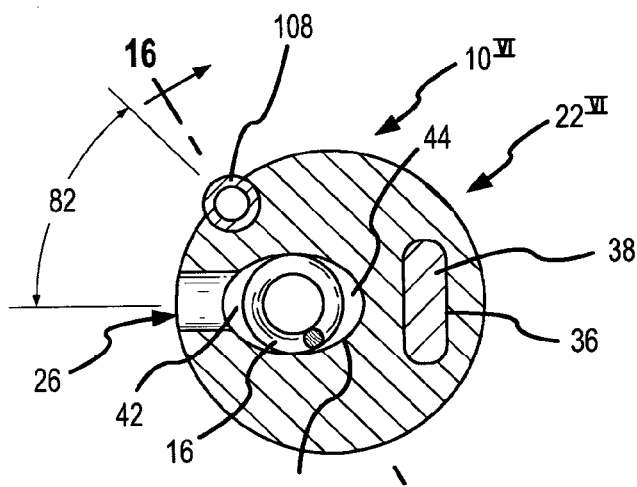
FIG. 15 is a cross-sectional view of the bipolar, virtual-electrode catheter according to the sixth embodiment of the present invention, taken along line 15-15 of FIG. 14.
Figure 16:
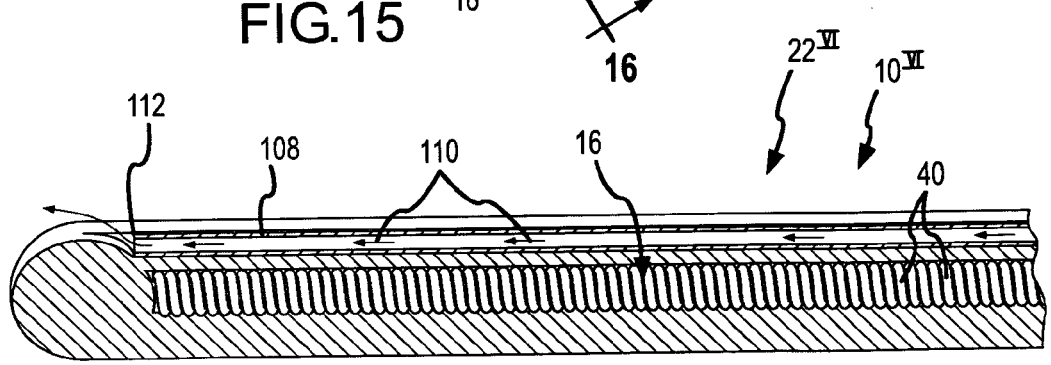
FIG. 16 is a fragmentary, cross-sectional view of the bipolar, virtual-electrode catheter according to the sixth embodiment of the present invention, taken along line 16-16 of FIG. 15.

FIGS. 14-16 depict a distal portion $22^{VI}$ sixth embodiment of the bipolar, virtual-electrode catheter $10^V$ according to the present invention. This embodiment $10^{VI}$ is similar to the first embodiment $10^{VI}$ (FIGS. 1-5) and the fifth embodiment $10^V$ (FIGS. 11-13). In this embodiment, however, the tubular surface electrode 108 is specifically configured to accommodate flow of a cooling fluid 110 through it. As is clearly visible from each of FIGS. 14-16, the tubular surface electrode 108 is hollow and thus able to accommodate the flow of a cooling fluid 110. As shown in FIGS. 14 and 16, the surface electrode tube 108 includes an open distal end or exit port 112. Thus, the fluid 110 flowing through the surface electrode tube can continue to flow and will not become stagnant. Since the surface electrode tube 108 is less likely to get hot in this embodiment that includes cooling fluid, no thermal sensors are depicted in FIGS. 14-16. However, thermal sensors may be juxtaposed adjacent to the surface electrode tube 108 if it remains desirable or preferable to monitor the temperature of the surface electrode tube during use of the bipolar, virtual-electrode catheter $10^{VI}$ according to this embodiment.

As suggested by FIG. 16, which is a cross-sectional view of a bipolar, virtual-electrode catheter $10^{VI}$ according to the sixth embodiment, taken along line 16-16 of FIG. 15, this embodiment may use two fluid sources (not shown). For example, a first saline source may supply cooling fluid 110 to the surface electrode tube 108, and a second fluid source may provide conductive fluid 34 (see e.g., FIG. 4) to the elliptical internal lumen 18 in which the large internal coil 16 depicted in FIGS. 14-16 resides. The exit port 112 shown in FIGS. 14 and 16 may be somewhat constricted to control the rate of flow through the surface electrode tube 108. Since it is possible that the ablative energy (e.g., RF energy) being delivered to the conductive fluid 34 that ultimately departs the exit portholes 26 may reach the fluid 110 flowing through the exit port 112 of the surface electrode tube 18, having two separate fluid supply systems is desirable. In order to control the total amount of saline delivered into the patient's bloodstream 74 (FIGS. 24-26), however, it is desirable to balance the fluid exiting through the exit portholes 26 with the fluid 110 exiting through the surface electrode tube 108. For example, it may be desirable to restrict the total fluid entering the patient's bloodstream to 3-18 ml per minute for certain wattages or amounts of RF energy delivered.

With separate fluid sources, it also is possible to avoid an unintended short circuit. The fluid flowing through the surface electrode tube 108 is not being used as part of a virtual-electrode in this particular embodiment. This fluid is being used for cooling only. Thus, the surface electrode tube 108 acts as a "normal" electrode rather than a virtual electrode. Alternatively, a closed system may be used to deliver cooling fluid 110 to the surface electrode tube 108. In this closed system, cooling fluid 110 may be delivered to the surface electrode tube from the first fluid source, and then the same fluid may be returned to the first fluid source via a return tube or pathway (not shown). In contrast, an open system is used to deliver saline or other conductive fluid 34 out of the exit portholes 26, which are acting as part of a virtual electrode with cooling effects.

Although the fifth embodiment $10^V$ (FIGS. 11-13) and the sixth embodiment $10^{VI}$ (FIGS. 14-16) of the present invention each show only one surface electrode tube 106, 108 respectively, being used, the present invention contemplates the use of multiple surface electrode tubes, similar to the surface electrode coils that are described next in connection with, for example, FIGS. 17-23.

FIGS. 17-19 depict three views of a distal portion $22^{VII}$ of a multipolar, virtual-electrode catheter $12^I$ according to a seventh embodiment of the present invention. This embodiment $12^I$ is similar to the embodiment $10^I$ depicted in FIGS. 1-5. In the seventh embodiment, however, a first surface electrode 114 and a second surface electrode 116 are present. In the embodiment depicted in FIGS. 17-19, the first and second surface electrodes 114, 116 are small, longitudinally-extending coils that symmetrically straddle the porthole centerline 28 (see FIG. 19). As will be described further below in connection with FIGS. 25 and 26, this particular configuration provides additional options for the user of this virtual-electrode catheter $12^I$. Similar to what was previously discussed in connection with FIG. 3, the radial offset angles 118, 120 depicted in FIG. 18 are selected to facilitate desired, effective creation of one or more electric fields 72 in the tissue 54 being ablated (see FIGS. 25 and 26). These angles 118, 120 may be, for example, 45°.

Figure 20:
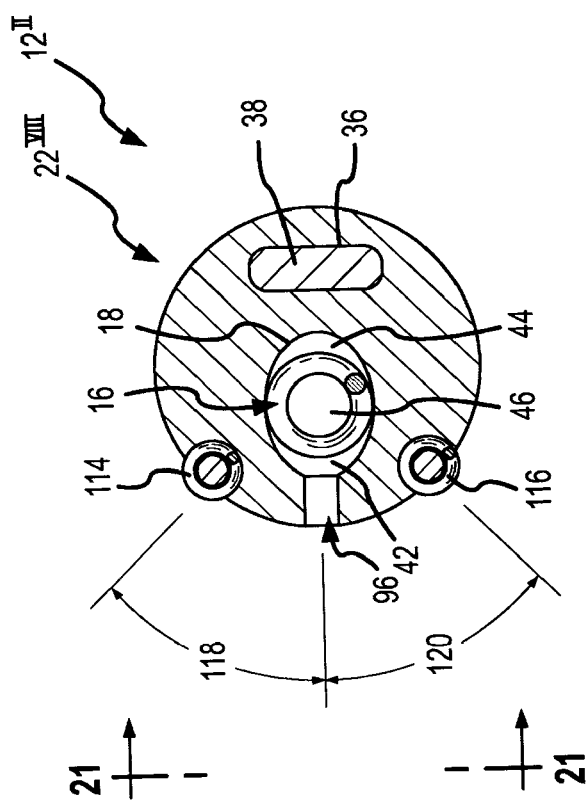
FIG. 20 is similar to FIG. 18, but depicts a cross-sectional view of a multipolar, virtual-electrode catheter according to an eighth embodiment of the present invention.
Figure 21:
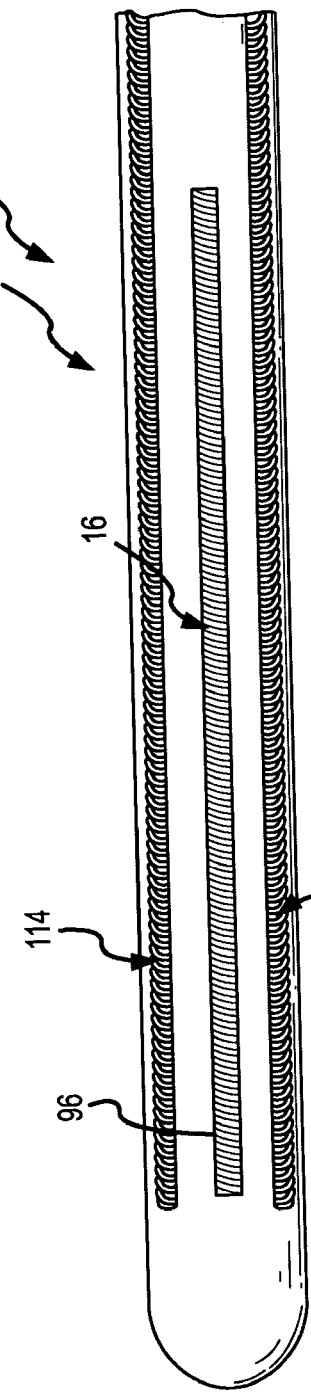
FIG. 21 is similar to FIG. 19, but depicts a fragmentary, front elevation of the multipolar, virtual-electrode catheter according to the eighth embodiment of the present invention, taken in the direction of line 21-21 of FIG. 20.

FIGS. 20 and 21 are similar to FIGS. 18 and 19, respectively, but depict a distal portion $22^{VIII}$ of a multipolar, virtual-electrode catheter according to an eighth embodiment $12^{II}$ of the present invention. In this eighth embodiment $12^{II}$, the exit portholes 26 have been replaced by an exit slot 96. In all other aspects, the eighth embodiment $12^{II}$ is similar to the previously-discussed embodiments.

Figure 22:
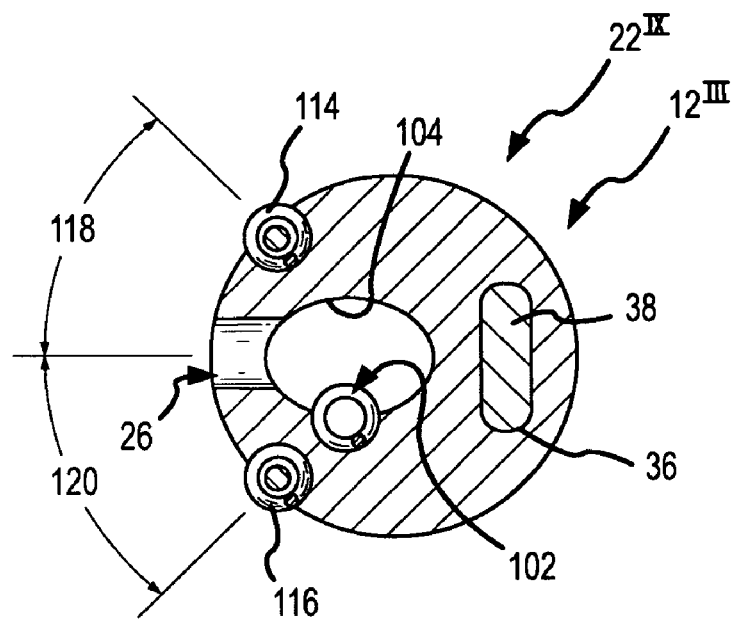
FIG. 22 is similar to FIG. 18, but depicts a cross-sectional view of a multipolar, virtual-electrode catheter according to a ninth embodiment of the present invention.

FIG. 22 is a cross-sectional view of a distal portion $22^{IX}$ of a multipolar, virtual-electrode catheter $12^{III}$ according to a ninth embodiment of the present invention. The ninth embodiment $12^{III}$ is similar to the seventh embodiment $12^{I}$ (see FIGS. 17-19). In the ninth embodiment $12^{III}$, however, the large internal coil electrode 16 has been replaced by a small internal coil electrode 102, similar to the small internal coil electrode 102 depicted in FIGS. 9 and 10 and discussed further above.

Figure 23:
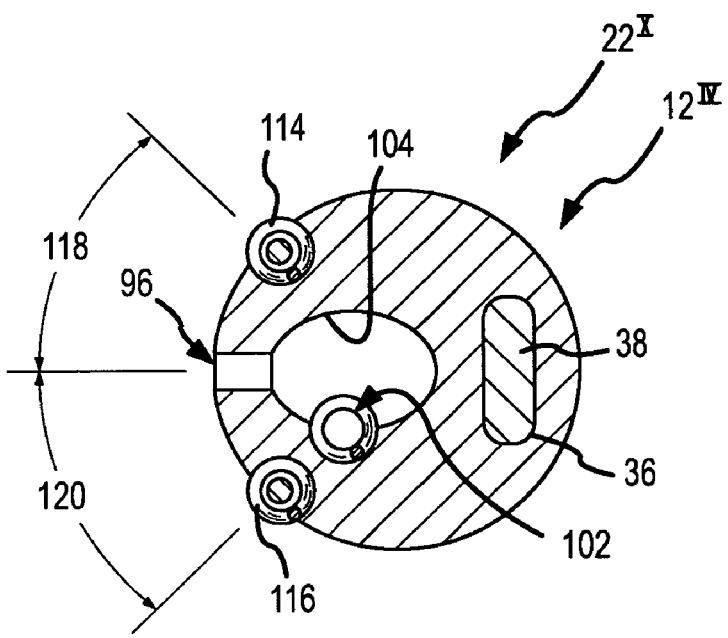
FIG. 23 is similar to FIG. 20, but depicts a cross-sectional view of a multipolar, virtual-electrode catheter according to a tenth embodiment of the present invention.

FIG. 23 is a cross-sectional view of a distal portion $22^{X}$ of a multipolar, virtual-electrode catheter $12^{IV}$ according to a tenth embodiment of the present invention. The tenth embodiment $12^{IV}$ of the virtual-electrode catheter is similar to the eighth embodiment $12^{II}$ (see FIGS. 20 and 21), but the large internal coil electrode 16 has been replaced with a small internal coil electrode 102. The small internal coil electrode 102 depicted in FIG. 23 is similar to the small internal coil electrode previously discussed in connection with FIGS. 9 and 10.

As mentioned, the surface electrode tubes 106, 108 depicted in, for example, FIGS. 11 and 14, respectively, may be used in place of the surface electrode coils 114, 116 depicted in FIGS. 17-23.

Figure 24:
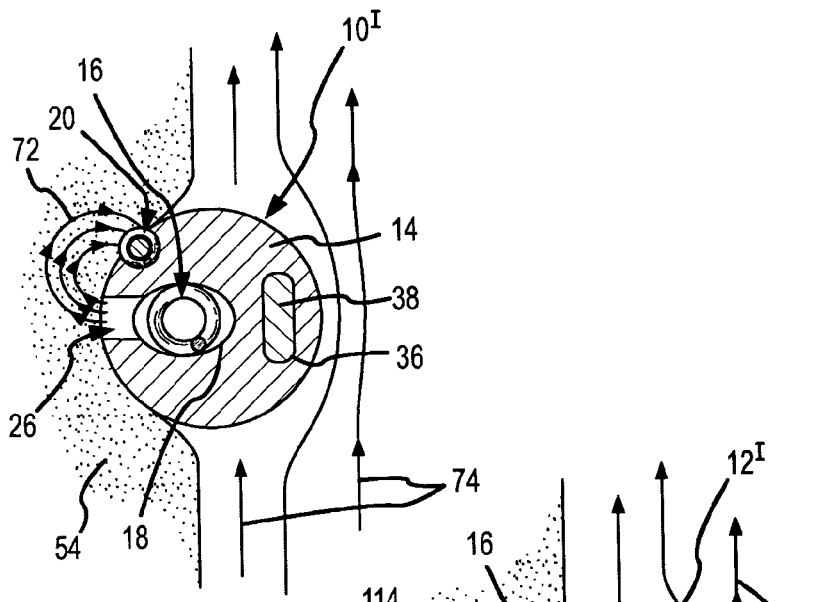
FIG. 24 is a fragmentary, cross-sectional view of the bipolar, virtual-electrode catheter depicted in FIGS. 1-5 being used to treat tissue.

FIG. 24 is a fragmentary, cross-sectional view of the virtual-electrode catheter $10^{I}$ depicted in FIGS. 1-5 during operation. In particular, FIG. 24 is a cross-sectional view of the distal portion of the bipolar, virtual-electrode catheter $10^{I}$ according to the first embodiment of the present invention being pressed against tissue 54 during lesion formation. The portion of the catheter that is not against the tissue is surrounded by blood that is represented schematically in FIG. 24 by the lines 74. As shown in FIG. 24, when the active electrode, which in this embodiment is the large internal coil 16, is activated, an electric field 72 is created that extends between the exit portholes 26 and the surface electrode 20. This electric field 72 passes through the tissue 54 to create the desired lesion. In particular, during operation, conductive fluid 34 (see e.g., FIG. 4) flowing through the elliptical internal lumen 18 is in contact with the active electrode (i.e., the large internal coil 16). The large internal coil 16, together with the conductive fluid, thus acts as a virtual electrode with the conductive fluid carrying the ablative energy (e.g., the RF energy) to the tissue 54 via the electric field 72 that is established between the active electrode (i.e., the large internal coil 16) and the passive electrode (i.e., the surface electrode 20).

Figure 25:
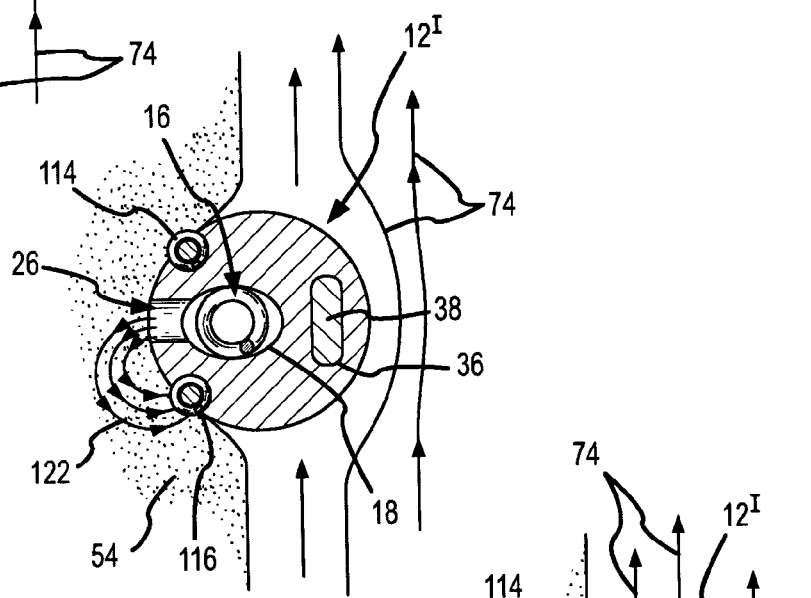
FIG. 25 is a fragmentary, cross-sectional view of the multipolar, virtual-electrode catheter depicted in FIGS. 17-19 being used to treat tissue in a first operating mode.

FIG. 25 is similar to FIG. 24, but depicts the multipolar, virtual-electrode catheter $12^{I}$ according to the seventh embodiment of the present invention (see FIGS. 17-19) in contact with the tissue to be ablated. In FIG. 25, this virtual-electrode catheter $12^{I}$ is operating in a first mode. In this first mode, a first electric field 122 is established between the large internal coil 16 and only one of the surface electrodes 116. Thus, in this first mode, the virtual-electrode catheter $12^{I}$ would create a lesion that is similar to the lesion being created in FIG. 24.

Figure 26:
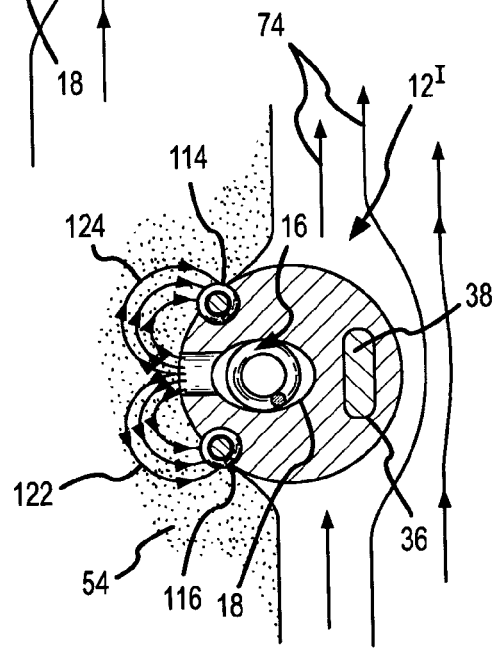
FIG. 26 is a fragmentary, cross-sectional view of the multipolar, virtual-electrode catheter depicted in FIGS. 17-19 being used to treat tissue in a second operating mode.

FIG. 26 also depicts the multipolar, virtual-electrode catheter $12^{I}$ of FIGS. 17-19. In FIG. 26, however, the virtual-electrode catheter $12^{I}$ is operating in a second mode. In this second mode, a first electric field 122 is established between the large internal coil 16 and one of the surface electrodes 116, and a second electric field 124 is established between the large internal coil 16 and the other surface electrode 114. Thus, the lesion being formed is potentially a larger lesion than may be formed in the first operating mode of this virtual-electrode catheter $12^{I}$ (see FIG. 25) or when using the first embodiment of the catheter $10^{I}$ (see FIG. 24).

Although ten embodiments of this invention have been described above with a certain degree of particularly, those skilled in the art could make numerous alterations to the disclosed embodiments without departing from the spirit or scope of this invention. For example, as mentioned above, the surface electrode tube 106 depicted in FIGS. 11-13, or the surface electrode tube 108 depicted in FIGS. 14-16, could be used in place of the surface electrode coils 20, 114, 116 depicted in the other figures. Also, although portholes 26 with circular cross sections and longitudinally-extending slots 96 are depicted in the figures for all of the embodiments described above, the "exit opportunities" may comprise other shapes and sizes, for example, micro-pores or holes with other than circular cross sections may be used. If properly configured, for example, micro-pores may be used to establish the desired flow characteristics for the conductive fluid 34 as it exits the distal portion of the virtual-electrode catheter. Further, although the catheter body is depicted in all of the figures with a circular cross section, the catheter body need not have a circular cross section. Also, the virtual-electrode catheter may comprise additional surface electrodes and may comprise more than one internal fluid lumen. Among the advantages of the instant invention over the prior art are (i) improved efficiency of RF ablation; (ii) improved efficiency of RF ablation using virtual-electrode technology; (iii) the ability to localize RF energy delivery to tissue; (iv) the ability to form lesions using low RF power; and (v) the ability to form lesions while introducing a small volume of fluid into a patient during lesion formation. Using the embodiments described above, for example, lesions may be obtained at low powers (e.g., 10 to 30 watts) and low fluid flow rates (e.g., 3 to 6 ml per minute through the internal lumen). All directional references (e.g., upper, lower, upward, downward, left, right, leftward, rightward, forward, rearward, top, bottom, above, below, vertical, horizontal, clockwise, and counterclockwise) are only used for identification purposes to aide the reader's understanding of the present invention, and do not create limitations, particularly as to the position, orientation, or use of the invention. It is intended that all matter contained in the above description or shown in the accompanying drawings shall be interpreted as illustrative only and not limiting. Changes in detail or structure may be made without departing from the spirit or scope of the invention as defined in the appending claims.

What is claimed is:

1. A virtual-electrode catheter for treatment of tissue, the catheter comprising:
   a catheter body comprising a sidewall and an outer surface;
   a first internal lumen extending within said catheter body and adapted to flowingly receive a conductive fluid;
   an exit feature comprising a flow path from said first internal lumen through said catheter body sidewall and said outer surface, said exit feature being adapted to permit the conductive fluid to exit from said first internal lumen toward the tissue;

an internal flexible conductor mounted within said first internal lumen adjacent to said exit feature and an inner surface of said catheter body sidewall, wherein said internal flexible conductor is adapted to deliver treatment energy to the tissue via the conductive fluid in said first internal lumen, wherein said internal flexible conductor is configured to be connected to an energy source to supply the treatment energy; and at least one surface electrode mounted on said outer surface of said catheter body adjacent to said exit feature, wherein the at least one surface electrode is configured to be connected to a return end of the energy source, wherein the internal flexible conductor operates as an active electrode when connected to the energy source, wherein the at least one surface electrode operates as an inactive return electrode to capture and return at least a portion of the treatment energy to the energy source when the at least one surface electrode is connected to the return end of the energy source, thereby creating an electric field between the internal flexible conductor and the at least one surface electrode, and wherein said at least one surface electrode comprises:

a first surface electrode comprising a first conductive coil along a first side of a longitudinal centerline of said exit feature; and a second surface electrode comprising a second conductive coil along a second side of said longitudinal centerline of said exit feature;

wherein said first conductive coil and said second conductive coil straddle said exit feature longitudinal centerline.

2. The virtual-electrode catheter of claim 1, wherein said exit feature is selected from the group consisting of a plurality of exit portholes, at least one exit slot, and a plurality of micro-pores.

3. The virtual-electrode catheter of claim 2, wherein said exit feature comprises a plurality of exit portholes arranged along said outer surface of said catheter body.

4. The virtual-electrode catheter of claim 3, wherein said exit feature longitudinal centerline comprises a porthole centerline, and wherein said plurality of exit portholes are symmetrically distributed about said porthole centerline.

5. The virtual-electrode catheter of claim 4, wherein said internal flexible conductor comprises an internal coil electrode, and wherein said internal coil electrode extends adjacent to each exit porthole of said plurality of exit portholes.

6. The virtual-electrode catheter of claim 5, wherein said internal coil electrode comprises a multitude of turns; wherein said multitude of turns of said internal coil electrode are adapted to allow the conductive fluid to pass between adjacent turns; and wherein at least two of said multitude of turns of said internal coil electrode are present between adjacent portholes of said plurality of exit portholes.

7. The virtual-electrode catheter of claim 4, wherein said porthole centerline extends longitudinally along said outer surface of said catheter body.

8. The virtual-electrode catheter of claim 2, wherein said exit feature comprises an exit slot extending longitudinally along said outer surface of said catheter body.

9. The virtual-electrode catheter of claim 8, wherein said internal flexible conductor comprises an internal coil electrode, and wherein said internal coil electrode extends over an entire length of said exit slot.

10. The virtual-electrode catheter of claim 1, wherein said internal flexible conductor comprises an internal coil electrode having a multitude of turns; and wherein said multitude of turns of said internal coil electrode are adapted to allow the conductive fluid to pass between adjacent turns.

11. The virtual-electrode catheter of claim 1, wherein said internal flexible conductor is selected from the group consisting of a coil electrode, a wire strand electrode, and a tubular electrode.

12. The virtual-electrode catheter of claim 11, wherein said internal flexible conductor is constructed from metal.

13. The virtual-electrode catheter of claim 11, wherein said internal flexible conductor comprises a coil electrode having an annular cross-sectional shape, wherein said first internal lumen has an elliptical cross-sectional shape, wherein said coil electrode extends longitudinally within said first internal lumen, and wherein a minor axis of said elliptical cross-sectional shape of said first internal lumen is substantially the same length as an outside diameter of said annular cross-sectional shape of said coil electrode.

14. The virtual-electrode catheter of claim 13, wherein a lateral cross section of said coil electrode and said first internal lumen defines a flow channel comprising a circular central region, a forward crescent-moon-shaped region, and a rearward crescent-moon-shaped region.

15. The virtual-electrode catheter of claim 1, wherein said internal flexible conductor comprises an internal coil electrode having a multitude of turns, wherein said internal coil electrode extends longitudinally within said first internal lumen, and wherein said internal coil electrode is at least partially embedded in a longitudinally-extending internal sidewall of said first internal lumen.

16. The virtual-electrode catheter of claim 1, wherein said surface electrode is constructed from metal.

17. The virtual-electrode catheter of claim 1, wherein said at least one surface electrode is mounted in and retained by a longitudinally-extending, C-shaped channel on said outer surface of said catheter body.

18. The virtual-electrode catheter of claim 1, wherein said first conductive coil is thermally and electrically conductive, and wherein said catheter further comprises a thermal sensor within said first conductive coil.

19. The virtual-electrode catheter of claim 1, wherein said at least one surface electrode is a cooled electrode.

20. The virtual-electrode catheter of claim 19, wherein said at least one surface electrode comprises a coil of wound, tubular metal adapted to carry a cooling fluid.

21. The virtual-electrode catheter of claim 1, wherein said at least one surface electrode acts as a dispersive electrode.

22. The virtual-electrode catheter of claim 1, wherein said first conductive coil is thermally and electrically conductive, and wherein said catheter further comprises a longitudinally-extending thermal sensor that extends within said first conductive coil.

23. The virtual-electrode catheter of claim 1, wherein said catheter further comprises at least one temperature sensor on said outer surface of said catheter body next to said at least one surface electrode.

24. The virtual-electrode catheter of claim 23, wherein said at least one temperature sensor is selected from the group consisting of a thermocouple, a thermister, and a fiber optic sensor.

25. The virtual-electrode catheter of claim 1, wherein said at least one surface electrode is metal, and wherein said internal flexible conductor is metal.

26. The virtual-electrode catheter of claim 1, wherein said virtual-electrode catheter further comprises a terminal sphere, and wherein said internal flexible conductor comprises a distal projection that is anchored to said terminal sphere.

27. The virtual-electrode catheter of claim 26, wherein said virtual-electrode catheter further comprises a release hole that extends from said first internal lumen through said terminal sphere and through said outer surface of said catheter body, and wherein said release hole is adapted to inhibit stagnation of said conductive fluid.

28. The virtual-electrode catheter of claim 1, wherein said catheter body defines a second longitudinally-extending internal lumen adapted to slippingly receive a rail.

29. The virtual-electrode catheter of claim 28, wherein said rail comprises a nickel-titanium wire.

30. The virtual-electrode catheter of claim 28, wherein said rail has a rounded-rectangular cross-sectional configuration that complements a cross-sectional configuration of said second lumen.

31. The virtual-electrode catheter of claim 1, wherein said internal flexible conductor has a tight spring pitch with individual coils that are closely packed 32. The virtual-electrode catheter of claim 31, wherein the individual coils regulate fluid flow within the first internal lumen and out of the exit feature.

33. The virtual-electrode catheter of claim 31, wherein the individual coils stretch and relax under tension and compression to affect fluid flow as a distal portion virtual-electrode catheter is manipulated during use.

34. The virtual-electrode catheter of claim 31, wherein gaps between adjacent individual coils change in size slightly to create pressure gradients in flow distribution along the exit features.

35. The virtual-electrode catheter of claim 31, wherein gaps between adjacent individual coils change in size slightly to affect impedance and heating of the conductive fluid.

36. The virtual-electrode catheter of claim 1, wherein said internal flexible conductor comprises turns which form a hollow portion along a center axis of the internal flexible conductor.

37. A virtual-electrode catheter for tissue ablation, the catheter comprising:
a catheter body having an outer surface, an internal lumen, and a fluid exit feature extending between said internal lumen and said outer surface, wherein said fluid exit feature is arranged along a longitudinally-extending exit feature centerline, wherein said exit feature is adapted to be placed against tissue, and wherein said internal lumen is adapted to deliver conductive fluid to said fluid exit feature;
an active internal electrode mounted within said internal lumen of said catheter body and adapted to contact said conductive fluid, wherein said active internal electrode is configured to be electrically connected to a source of ablative energy and is adapted to impart said ablative energy to the tissue via said conductive fluid; and
at least one passive external electrode mounted on said outer surface of said catheter body adjacent to said fluid exit feature, wherein said at least one passive external electrode is configured to be electrically connected to said source of ablative energy to return at least a portion of said ablative energy to said source of ablative energy, whereby, upon activation of said source of ablative energy, an electric field is created between said active internal electrode and said at least one passive external electrode, and in the tissue adjacent to said fluid exit feature; wherein said at least one passive external electrode further comprises:
a first surface electrode mounted on said outer surface of said catheter body adjacent to a first side of said longitudinally-extending exit feature centerline; and
a second surface electrode mounted on said outer surface of said catheter body adjacent to a second side of said longitudinally-extending exit feature centerline.

38. A multipolar, virtual-electrode catheter for performing radiofrequency ablation of cardiac tissue, the catheter comprising:
a catheter body defining an outer surface and an internal lumen, wherein said internal lumen is adapted to carry conductive fluid;
at least two metal electrodes positioned on said outer surface of said catheter body, wherein said at least two metal electrodes are adapted for placement against the cardiac tissue, wherein at least one of said at least two metal electrodes is configured to be connected to a return end of an RF source;
a metal conductor positioned within said internal lumen and adapted to impart radiofrequency energy to the conductive fluid, wherein said internal flexible conductor is configured to be connected to the RF source to supply the radiofrequency energy;
at least one opening on said outer surface of said catheter, said at least one opening adapted to create a flow path for the conductive fluid in said internal lumen to flow out of the catheter and impinge upon the cardiac tissue as a virtual-electrode, wherein said at least one opening is arranged along a longitudinally-extending opening centerline, and wherein said at least two metal electrodes further comprise:
a first surface electrode mounted on said outer surface of said catheter body adjacent to a first side of said longitudinally-extending opening centerline; and
a second surface electrode mounted on said outer surface of said catheter body adjacent to a second side of said longitudinally-extending opening centerline; and
at least one temperature sensor on said outer surface of said catheter body in close juxtaposition to said at least two metal electrodes, wherein the internal flexible conductor operates as an active electrode when connected to the RF source, wherein at least one of the at least two metal electrodes operates as an inactive return electrode to capture and return at least a portion of the RF energy to the RF source when the at least one of the at least two metal electrodes is connected to the return end of the RF source, thereby creating an electric field between the metal conductor and at least one of the first surface electrode and the second surface electrode.

39. The multipolar, virtual-electrode catheter of claim 38, further comprising a shaping wire provided separate from the metal conductor.

* * * * *